US00PP08014P

United States Patent [19]

Imazio

[11] Patent Number: Plant 8,014

[45] Date of Patent: Oct. 27, 1992

[54] HEATH PLANT NAMED HEIDI

[75] Inventor: Bruno L. Imazio, Watsonville, Calif.

[73] Assignee: Bay City Flower Co., Half Moon Bay, Calif.

[21] Appl. No.: 697,789

[22] Filed: May 9, 1991

[51] Int. Cl.[5] ..... A01H 5/00

[52] U.S. Cl. ..... Plt./54.1

[58] Field of Search ..... Plt./54

*Primary Examiner*—James R. Feyrer

*Attorney, Agent, or Firm*—James R. Cypher

[57] ABSTRACT

A new and distinct variety of heath named 'Heidi', a seedling of unknown pollen parent discovered growing in a field of Erica persoluta 'Sunset', the variety believed to be the seed parent, which is principally distinguished by its dwarfish growth habit which makes it suitable for pot plant culture relative to that of its parent, which is of the cut flower variety. The new variety is also distinguished by its red-purple magenta colored blooms, its natural abundant branching, its stiff erect stems, its compact, dense appearance, and its early blooming time of mid January through mid February which makes it available for the Valentine Day market.

1 Drawing Sheet

BACKGROUND OF THE INVENTION

This invention relates to a new and distinct plant variety of the Ericaceae family which has been named Erica persoluta 'Heidi' by the assignee of the invention. This new heather variety was discovered by the inventor as a seedling of unknown pollen parentage growing in a cultivated field of Erica persoluta 'Sunset' (U.S. Plant Pat. No. 5,336), the cut-flower variety believed to be the seed parent, where it was noticed because of its intense red-purple, magenta colored blooms, and dwarfish growth habit compared to the field cut flower heath varieties, which make it desirable for potted plant culture. The new variety resembles its seed parent persoluta 'Sunset' in its early blooming habit.

The characteristics of the new variety that make it desirable for potted plant culture are: its slower growth rate and natural branching with little or no pruning which results in a shorter plant with a full dense appearance.

The closest varieties of heath, cultivated as potted plants, of which I am aware are Erica persoluta and Erica persoluta 'Rosemarie'. 'Heidi' and 'Rosemarie' are very similar in their dwarfish growth habit which differs greatly from the growth habit of Erica persoluta. These growth habit characteristics are:

1. slower growth rate and shorter height,
2. compact, dense appearance, and
3. natural abundant branching with minimal or no pruning.

In bloom color, 'Heidi' is darker in color than 'Rosemarie' and lighter in color than Erica persoluta.

In blooming time, at Half Moon Bay, Calif., 'Heidi' starts to bloom 1 to 2 weeks later than 'Rosemarie', and 1 to 2 months earlier than Erica persoluta. 'Heidi' normally reaches bloom maturity from mid January through mid February, and 'Rosemarie' reaches bloom maturity from December through February. This makes 'Heidi' and 'Rosemarie' available for the Valentine Day market. Erica persoluta does not reach bloom maturity until March.

'Heidi' also differs from 'Rosemarie' in its darker green foliage color during the vegatative stage, and its distinct tight plumed foliage having very erect and stiff stems. 'Rosemarie' has needlelike foliage and stems that give a much looser appearance.

Asexual reproduction of the new cultivar through successive generations by means of cuttings performed under the direction and control of the inventor at Half Moon Bay, shows that its shorter, compact growth habit, natural abundant branching, early blooming time and intense red-purple color, remain true from generation to generation and appear to be firmly fixed.

BRIEF DESCRIPTION OF THE DRAWING

The accompanying drawing is a color photograph of a potted plant of the new variety illustrating the overall appearance and form of the plant, shorter height, dense compact appearance and intense red-purple blooms.

DETAILED DESCRIPTION OF THE DRAWING

The following is a detailed description of the new variety with color designations according to the R.H.S. Colour Chart published by The Royal Horticultural Society of London, England. The following description is based on observations of well fertilized 4" potted plants of 12 to 14 months of age from initial propagation which were grown outside under saran in a commercial nursery at Half Moon Bay, Calif., where temperatures average from 55 to 65 degrees F. during the summer months, and 45 to 55 degrees F. during the winter months.

Color designation and other values stated may deviate slightly from the stated values from flowering to flowering, but the deviations will be within the range expected from varying environmental, seasonal, and cultural conditions.

The Plant

Origin: Seedling.

Parentage:

*Seed parent.*—Erica persoluta 'Sunset'.

*Pollen parent.*—Unknown.

Classification:

*Botanic.*—Erica persoluta 'Heidi'.

*Commercial.*—'Heidi'.

Form: Perennial.

Shape: Upright, stems curving slightly to accommodate fullness of plant.

Height: Mean 11" to 12".

Girth: Mean 5".

Branching: Naturally abundant with minimal or no pruning necessary.

Growth: Slow growth rate resulting in reduced height of plant.

Rooting time: 3 weeks.

Foliage: Abundant, with distinct tight plumed foliage, very erect and stiff.

*Size of leaf.*—Mean ⅛" long and less than 1/16" wide.

*Shape of leaf.*—Plumedlike.

*Character.*—Sulcate.

*Color.*—RHS 143A.

*Texture.*—Smooth.

Hardiness: Can tolerate a temperature range of 28 to 100 degrees F.

Disease resistance: Considerable resistance to fungus type diseases. Common diseases include phythium and phytoplhora.

Seed production: Sparce; commercially produced asexually by cuttings.

Effects of weather: Can tolerate freezing temperatures for one week. Over 90 degree F. temperatures stress the plant.

In general, the foliage is too tiny to determine further characteristics by on plant observation.

The Bud

Size:

*Length.*—⅛" and less.

*Diameter.*—1/16" and less.

Rate of opening: Rapid, progressive and continuous beginning at the base of stem and progressing to the tip of the stem.

Petals: Corolline flowers in which the sepals are relatively insignificant.

Color: R.H.S. 72C.

Inflorescence

Blooming habit: Annually, from mid January through mid February.

Size of bloom: ⅛" by 1/16".

Borne: Compound raceme. Clusters with as many as seven terminal buds.

Shape: Urceolate.

Appearance: Satiny.

Color: RHS 71C to 71D in overall appearance of the plant.

Flower Stem:

*Length.*—Mean ¼" to 3".

*Color.*—RHS 177D.

*Strength.*—Woody and supple.

Discoloration: Does not fade.

Effects of weather: Prolonged exposure to hot or wet weather is detrimental to plant appearance. Extended periods of hot dry sunshine will accelerate blooming and cause blooms to fade and decline more quickly, shortening its lasting quality. Extended wet weather will cause more mature blooms in the clusters to turn brown.

Persistence: Blooms persists long after the stem ceases to draw water. Blooms do not shed easily.

Fragrance: Mild.

Lasting quality: On plant: 2 months. As a cut flower: 2 weeks.

The outstanding characteristics of this new plant resides in its early blooming from mid January through mid February for the Valentine's Day market, whereas Erica persoluta does not begin to bloom until March. Its natural compact growth habit makes it suitable for pot plant culture, whereas its parent Erica persoluta 'Sunset' is of the cut flower variety and is taller.

TABLE OF COMPARISON

| PLANT | NEW CULTIVAR | 'ROSE-MARIE' | *ERICA PERSOLUTA* |
|---|---|---|---|
| Height | a 4" pot will be 8" or 9" high in 18 mos. growing time with little or no pruning | Same | a 4" pot will be 10" to 12" high in 18 mos growing time with numerous pruning. |
| Form | short, dense appearing, compact woody shrub | Same | woody shrub |
| Shape | Upright, stems curving slightly to accomodate fullness of plant | Same | Upright, stems spreading to produce fullness of plant |
| Branch-ing | naturally generous, minimal or no pruning needed | Same | Generous, several prunings necessary to encourage branching |
| Growth | upright but naturally short and branching with woody, flexible strength | Same | upright with woody flexible strength |
| Blooming Season: | Annual, mid January through mid February | annual, Dec. thru Feb. | Annual, early March through late March |
| Foliage | | | |
| Color | R.H.S. 143A | R.H.S. 144A | R.H.S. 143A with 59A streaking through the leaves. |
| Size | 1/8" | Same | Same |
| Shape | plumedlike, with stiff, erect stems | Acerose and stems give a loose appearance | Acerose |
| Quantity | Abundant | Same | Same |
| Bloom | | | |
| Size | 1/8" × 1/16" | Same | 3/16" × 1/16" |
| Shape | Urceolate | Same | Ovoid |
| Color | R.H.S. 71C to 71D | R.H.S. 66D | R.H.S. 70A to 70B |
| Rate of opening: | Rapid, progressive and continuous beginning at the base of the stem and progressing to the tip of the stem. | Same | Same |

I claim:

1. A new and distinct hybrid plant variety of the Heath family substantially as herein shown and described.

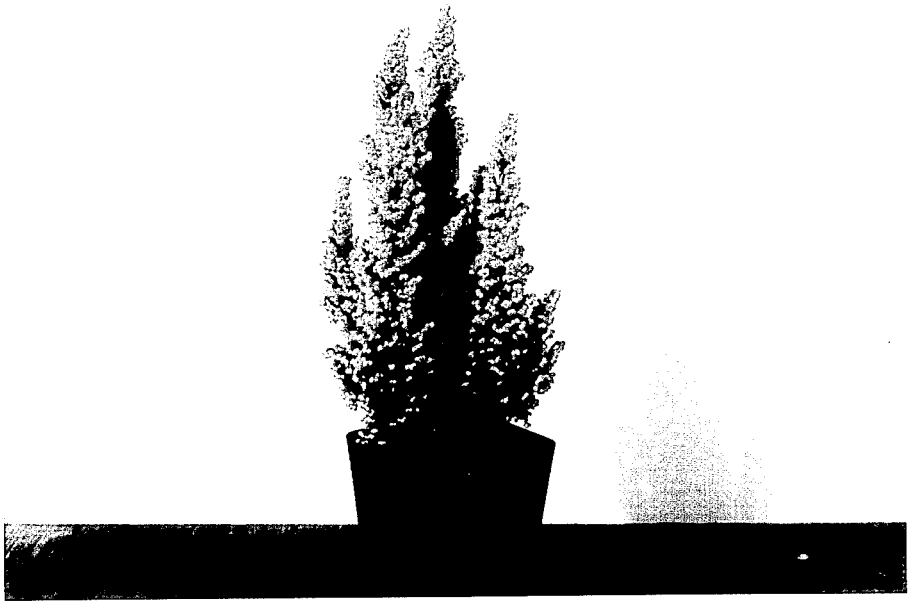

* * * * *